(12) United States Patent
Fenner et al.

(10) Patent No.: US 11,725,995 B2
(45) Date of Patent: Aug. 15, 2023

(54) PRESSURE SENSOR ASSEMBLY FOR USE IN IMPLANTABLE MEDICAL DEVICE INCLUDING A SUBSTRATE HAVING VIA THAT EXTENDS THROUGH SUBSTRATE ALONG VIA AXIS BETWEEN FIRST MAJOR SURFACE AND SECOND MAJOR SURFACE OF SUBSTRATE

(71) Applicant: Medtronic, Inc., Minneapolis, MN (US)

(72) Inventors: Andreas Fenner, Chandler, AZ (US); David A. Ruben, Mesa, AZ (US); Andrew J. Ries, Lino Lakes, MN (US); Chetan Patel, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 20 days.

(21) Appl. No.: 17/571,825

(22) Filed: Jan. 10, 2022

(65) Prior Publication Data

US 2022/0244123 A1 Aug. 4, 2022

Related U.S. Application Data

(60) Provisional application No. 63/144,001, filed on Feb. 1, 2021.

(51) Int. Cl.
*G01L 9/00* (2006.01)
*H01L 23/00* (2006.01)
(Continued)

(52) U.S. Cl.
CPC ............ *G01L 9/0073* (2013.01); *B23K 26/20* (2013.01); *H01L 23/5226* (2013.01);
(Continued)

(58) Field of Classification Search
None
See application file for complete search history.

(56) References Cited

U.S. PATENT DOCUMENTS 5,535,752 A * 7/1996 Halperin .............. A61N 1/3655
600/483
6,968,743 B2 11/2005 Rich et al.
(Continued)

FOREIGN PATENT DOCUMENTS

EP 0757542 6/2000
WO 96/26674 9/1996

OTHER PUBLICATIONS

International Search Report and Written Opinion for PCT/US2022/014483, dated May 4, 2022; 9 pages.

*Primary Examiner* — Octavia Davis Hollington
*Assistant Examiner* — Jermaine L Jenkins

(57) ABSTRACT

Various embodiments of a pressure sensor assembly and an implantable medical device that includes such assembly are disclosed. The assembly includes a substrate having a via that extends through the substrate along a via axis between a first major surface and a second major surface of the substrate, a membrane disposed on the first major surface of the substrate and over the via, and a patterned metal layer disposed on a first major surface of the membrane, a portion of such layer including a first capacitor plate. The assembly further includes an integrated circuit disposed adjacent to the first major surface of the membrane and electrically connected to the metal layer. The integrated circuit includes a second capacitor plate disposed on or within a substrate of the integrated circuit. The first capacitor plate and the second capacitor plate form a variable capacitor disposed along the via axis.

20 Claims, 6 Drawing Sheets

(51) Int. Cl.
*H05K 5/06* (2006.01)
*A61B 5/0215* (2006.01)
*B23K 26/20* (2014.01)
*H01L 23/522* (2006.01)

(52) U.S. Cl.
CPC ............... *H01L 24/48* (2013.01); *H05K 5/06* (2013.01); *A61B 5/0215* (2013.01); *A61B 2562/0247* (2013.01)

(56) References Cited

U.S. PATENT DOCUMENTS

| | | |
|---|---|---|
| 7,591,185 B1 | 9/2009 | Mothilal et al. |
| 7,615,308 B2 | 11/2009 | Frederiksen et al. |
| 7,955,319 B2 | 6/2011 | Miesel |
| 9,265,428 B2 | 2/2016 | O'Brien et al. |
| 9,772,245 B2 * | 9/2017 | Besling ................ G01L 9/0045 |
| 10,124,559 B2 | 11/2018 | Sandlin et al. |
| 10,442,679 B2 * | 10/2019 | Boutaud ............... G01L 9/0042 |
| 2005/0229710 A1 * | 10/2005 | O'Dowd ............... G01L 9/0075 |
| | | 73/718 |
| 2007/0267708 A1 | 11/2007 | Courcimault |
| 2009/0145623 A1 | 6/2009 | O'Brien et al. |
| 2011/0066046 A1 | 3/2011 | Young et al. |
| 2012/0247218 A1 | 10/2012 | Crivelli |
| 2019/0350467 A1 | 11/2019 | Greenhut |
| 2020/0141818 A1 * | 5/2020 | Bao ........................... G01L 9/12 |
| 2021/0178518 A1 | 6/2021 | Ruben et al. |

\* cited by examiner

PRESSURE SENSOR ASSEMBLY FOR USE IN IMPLANTABLE MEDICAL DEVICE INCLUDING A SUBSTRATE HAVING VIA THAT EXTENDS THROUGH SUBSTRATE ALONG VIA AXIS BETWEEN FIRST MAJOR SURFACE AND SECOND MAJOR SURFACE OF SUBSTRATE

RELATED PATENT APPLICATION

This application claims the benefit of U.S. Provisional Patent Application Ser. No. 63/144,001, filed on Feb. 1, 2021, which is incorporated by reference herein in its entirety.

TECHNICAL FIELD

This disclosure generally relates to a pressure sensor assembly and more particularly to an implantable medical device that includes a pressure sensor assembly.

BACKGROUND

A variety of medical devices for delivering a therapy and/or monitoring a physiological condition have been clinically implanted or proposed for clinical implantation in patients. Such implantable medical devices can deliver electrical stimulation or drug therapy to, and/or monitor conditions associated with, the heart, muscle, nerve, brain, stomach or other organs or tissue, as examples. Implantable medical devices can include or be coupled to one or more physiological sensors, which can be used with the device to monitor signals related to various physiological conditions from which a patient state or the need for a therapy can be assessed.

Pressure sensors may be employed with implantable medical devices as physiological sensors configured to detect, e.g., changes in blood pressure. Example pressure sensors that may be useful for measuring blood pressure may employ capacitive, piezoelectric, piezoresistive, electromagnetic, optical, resonant-frequency, or thermal methods of pressure transduction.

SUMMARY

The techniques of this disclosure generally relate to a pressure sensor assembly and a device that utilizes such assembly. The assembly can include a substrate that has a via that extends through the substrate along a via axis between a first major surface and a second major surface of the substrate. A membrane can be disposed over the via, and a patterned metal layer can be disposed on the membrane. A portion of the metal layer can be aligned with the via along the via axis and provide a first capacitor plate. The assembly can further include an integrated circuit disposed over the via and electrically connected to the metal layer disposed on the membrane. The integrated circuit can include an integrated circuit substrate and a second capacitor plate disposed on or within the substrate. The second capacitor plate is substantially parallel to and spaced apart from the first capacitor plate disposed on the membrane. The first capacitor plate and the second capacitor plate can form a variable capacitor disposed along the via axis.

In one example, aspects of this disclosure relate to a pressure sensor assembly that includes a substrate having a via that extends through the substrate along a via axis between a first major surface and a second major surface of the substrate, where the via axis is substantially orthogonal to the first major surface of the substrate; a membrane that includes a first major surface and a second major surface, where the second major surface of the membrane is disposed on the first major surface of the substrate and over the via; and a patterned metal layer disposed on the first major surface of the membrane, where a portion of the metal layer aligned with the via along the via axis includes a first capacitor plate. The pressure sensor assembly further includes an integrated circuit disposed adjacent to the first major surface of the membrane and over the via, where the integrated circuit is electrically connected to the metal layer disposed on the first major surface of the membrane. The integrated circuit includes an integrated circuit substrate having a first major surface and a second major surface, and a second capacitor plate disposed on or within the substrate. The second capacitor plate is substantially parallel to and spaced apart from the first capacitor plate disposed on the membrane. The first capacitor plate and the second capacitor plate form a variable capacitor disposed along the via axis.

In another example, aspects of this disclosure relate to an implantable medical device that includes a housing and a pressure sensor assembly. The pressure sensor assembly includes a substrate having a via that extends through the substrate along a via axis between a first major surface and a second major surface of the substrate, where the via axis is substantially orthogonal to the first major surface of the substrate; a membrane that includes a first major surface and a second major surface, where the second major surface of the membrane is disposed on the first major surface of the substrate and over the via; and a patterned metal layer disposed on the first major surface of the membrane, where a portion of the metal layer aligned with the via along the via axis includes a first capacitor plate. The pressure sensor assembly further includes an integrated circuit disposed adjacent to the first major surface of the membrane and over the via, where the integrated circuit is electrically connected to the metal layer disposed on the first major surface of the membrane. The integrated circuit includes an integrated circuit substrate having a first major surface and a second major surface, and a second capacitor plate disposed on or within the substrate. The second capacitor plate is substantially parallel to and spaced apart from the first capacitor plate disposed on the membrane. The first capacitor plate and the second capacitor plate form a variable capacitor disposed along the via axis.

In another example, aspects of this disclosure relate to a method that includes disposing a membrane adjacent to a first major surface of a substrate; disposing a via through the substrate such that it extends along a via axis between the first major surface and a second major surface of the substrate, where the membrane is disposed over the via, and further where the via axis is substantially orthogonal to the first major surface of the substrate; and disposing a metal layer on the membrane such that the membrane is disposed between the metal layer and the substrate. The method further includes patterning the metal layer such that a portion of the metal layer forms a first capacitor plate that is aligned with the via along the via axis; disposing an integrated circuit adjacent to the membrane and over the via, where the integrated circuit is electrically connected to the metal layer, and further where the integrated circuit includes an integrated circuit substrate having a first major surface and a second major surface, and a second capacitor plate disposed on or within the substrate. The second capacitor plate is substantially parallel to and spaced apart from the first capacitor plate disposed on the membrane. Further, the first capacitor plate and the second capacitor plate form a variable capacitor disposed along the via axis.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 6A is a schematic cross-section view of disposing a membrane adjacent to a first major surface of a substrate and a nonconductive layer adjacent to a second major surface of the substrate; FIG. 6B is a schematic cross-section view of patterning the nonconductive layer; FIG. 6C is a cross-section view of disposing a via through the nonconductive layer and the substrate; FIG. 6D is a schematic cross-section view of disposing a metal layer on the membrane; FIG. 6E is a schematic cross-section view of patterning the metal layer; and FIG. 6F is a schematic cross-section view of disposing an integrated circuit adjacent to the membrane.

FIG. 7A is a schematic cross-section view of forming vias through a nonconductive layer and a substrate wafer; FIG. 7B is a schematic cross-section view of disposing a membrane wafer on a first major surface of a substrate wafer; FIG. 7C is schematic cross-section view of removing one or more portions of the membrane wafer; FIG. 7D is a schematic cross-section view of disposing a metal layer on the membrane wafer; FIG. 7E is a schematic cross-section view of patterning the metal layer; and FIG. 7F is a schematic cross-section view of disposing integrated circuits adjacent to the membrane wafer and singulating the substrate wafer and the membrane wafer to provide one or more pressure sensor assemblies 10.

DETAILED DESCRIPTION

Figure 1:
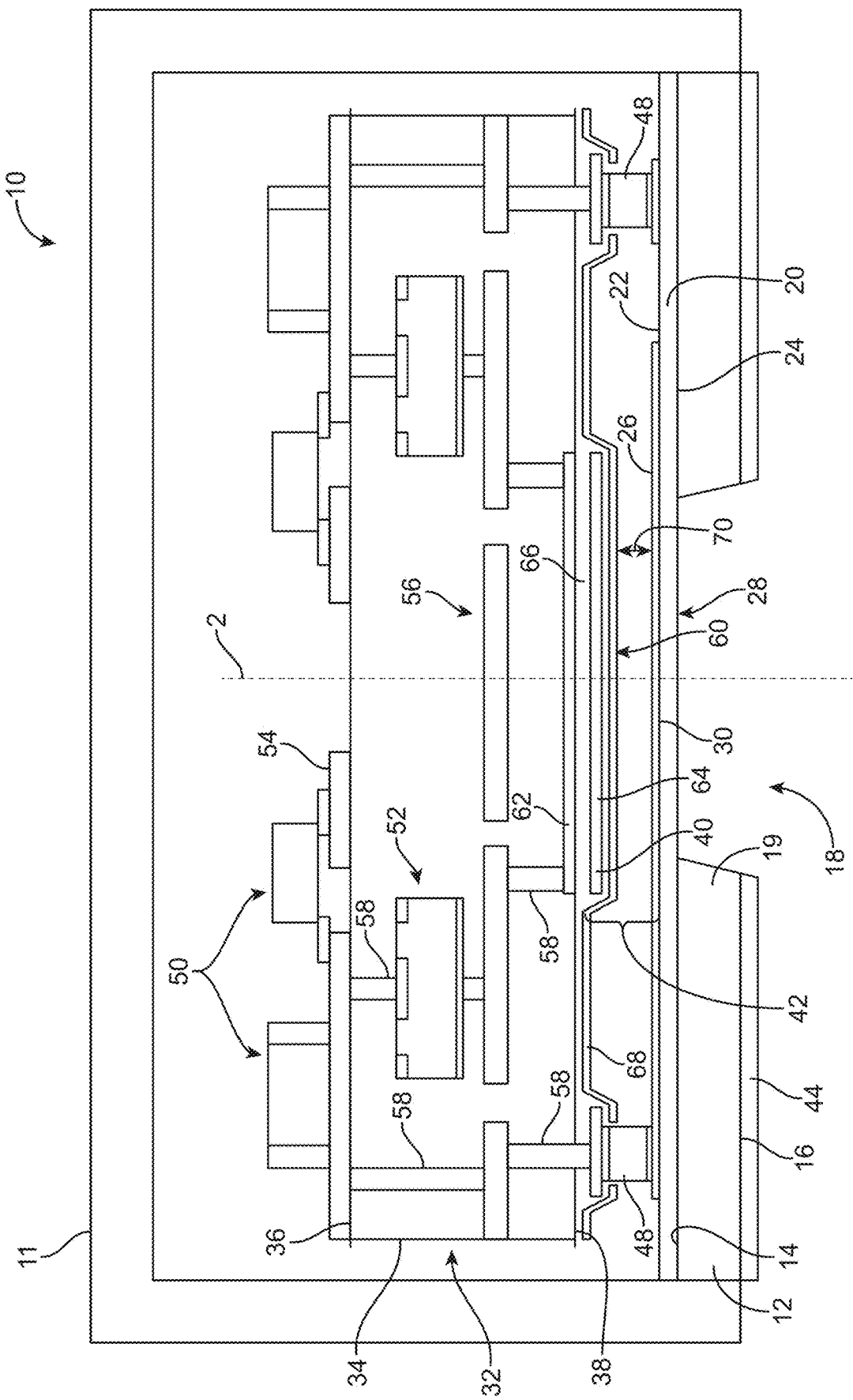
FIG. 1 is a schematic cross-section view of one embodiment of a pressure sensor assembly.

The techniques of this disclosure generally relate to a pressure sensor assembly and a device that utilizes such assembly. The assembly can include a substrate that has a via that extends through the substrate along a via axis between a first major surface and a second major surface of the substrate. A membrane can be disposed over the via, and a patterned metal layer can be disposed on the membrane. A portion of the metal layer can be aligned with the via along the via axis and provide a first capacitor plate. The assembly can further include an integrated circuit disposed over the via and electrically connected to the metal layer disposed on the membrane. The integrated circuit can include an integrated circuit substrate and a second capacitor plate disposed on or within the substrate. The second capacitor plate is substantially parallel to and spaced apart from the first capacitor plate disposed on the membrane. The first capacitor plate and the second capacitor plate can form a variable capacitor disposed along the via axis.

Low power pressure sensors such as capacitive pressure sensors can be utilized with implantable medical devices. Pressure sensors having smaller form factors may be needed for some implantable medical devices. A small form-factor pressure sensor may, however, have reduced capacitance, thereby making the sensor more sensitive to stray capacitance and variations caused by complex manufacturing processes that are required to make such sensor.

One or more embodiments of pressure sensor assemblies described herein exhibit one or more advantages over currently-available pressure sensors. For example, complex circuitry necessitated by smaller form factors can be disposed closer to a membrane of the sensor to minimize parasitic non-active circuit capacitance as well as reduce radio-frequency coupling into the circuitry. As a result, the pressure sensor can have a smaller form factor such that the sensor can be delivered into a body of a patient using, e.g., injection, catherization, or various out-patient procedures. Further, the pressure sensor may be made from biocompatible materials to reduce the need for use of protective films disposed around the sensor. Such protective films can induce stresses and non-linearities in the sensor. The membrane of the sensor can also form a portion of a housing of the sensor such that additional processes for attaching the membrane to the housing may not be required. Variability and non-linearities caused by package-induced stresses can be reduced by utilizing the membrane of the sensor to form at least a portion of the housing.

One or more embodiments of a pressure sensor described herein can include a variable capacitor connected to a membrane, where a capacitor plate of the variable capacitor is disposed on the membrane and the other capacitor plate can be disposed on or within an integrated circuit that is disposed adjacent to the membrane. The sensor can also include a reference capacitor that can be disposed within the integrated circuit. In one or more embodiments, a capacitor plate of the reference capacitor can function as a capacitor plate for the variable capacitor.

Further, one or more standoffs can be disposed between the integrated circuit and the membrane to provide a defined distance between the integrated circuit and the membrane. Such defined distance can provide a predictable nominal capacitance. In one or more embodiments, a hermetically-sealed space can be formed between the integrated circuit and the membrane, thereby preventing particles or contaminants from entering the space between the integrated circuit and the membrane.

Figure 2:
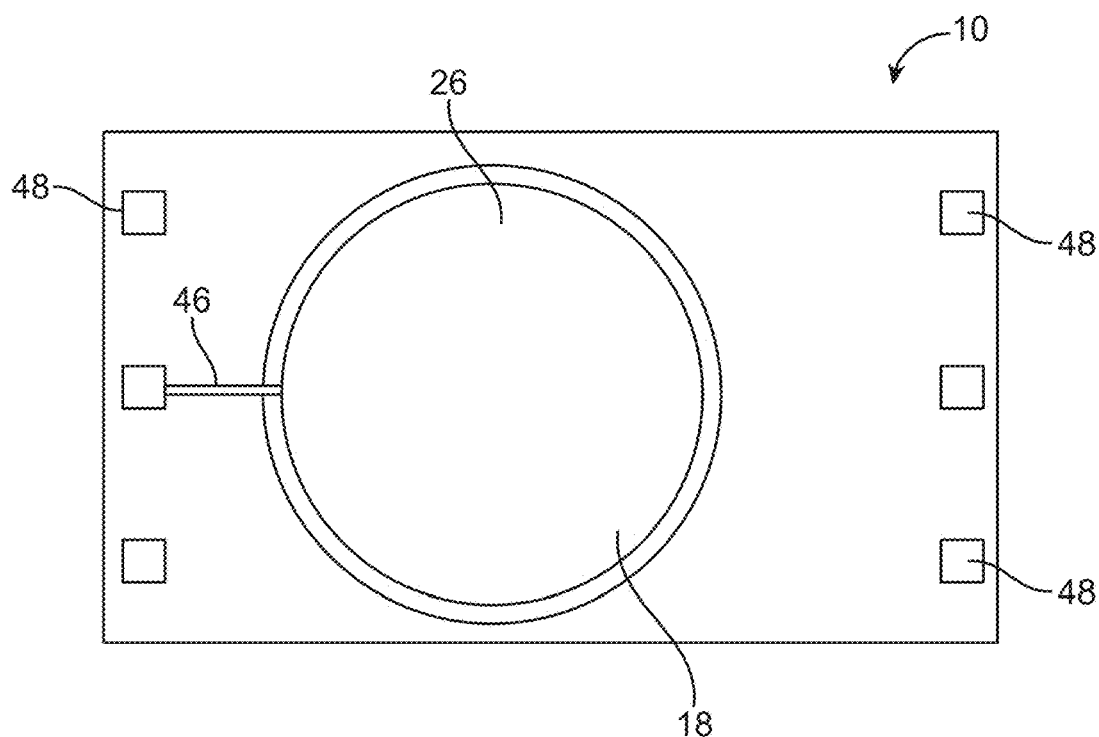
FIG. 2 is a schematic bottom plan view of the pressure sensor assembly of FIG. 1.

FIGS. 1-2 are schematic cross-section and plan views of one embodiment of a pressure sensor assembly 10. The assembly 10 includes a substrate 12 having a via 18 that extends through the substrate along a via axis 2 between a first major surface 14 and a second major surface 16 of the substrate. The via axis 2 is substantially orthogonal to the first major surface 14 of the substrate 12. The assembly 10 also includes a membrane 20 having a first major surface 22 and a second major surface 24, where the second major surface of the membrane is disposed on the first major surface 14 of the substrate 12 and over the via 18. A patterned metal layer 26 is disposed on the first major surface 22 of the membrane 20, where a portion 28 of the metal layer is aligned with the via 18 along the via axis 2 and forms a first capacitor plate 30. The assembly 10 further includes an integrated circuit 32 disposed adjacent to the first major surface 22 of the membrane 20 and over the via 18, where the integrated circuit is electrically connected to the metal layer 26 disposed on the first major surface 22 of the membrane 20. The integrated circuit 32 includes an integrated circuit substrate 34 having a first major surface 36 and a second major surface 38, and a second capacitor plate 40 disposed on or within the substrate, where the second capacitor plate is substantially parallel to and spaced apart from the first capacitor plate 30 disposed on the membrane 20. The first capacitor plate 30 and the second capacitor plate 40 form a variable capacitor 42 disposed along the via axis 2. The assembly can also include an enclosure 11 within which the integrated circuit 32 is disposed.

The pressure sensor assembly 10 can take any suitable shape or shapes and have any suitable dimensions. Further, the assembly 10 can be utilized with any suitable device or system as is further described herein.

The enclosure 11 can also take any suitable shape or shapes and have any suitable dimensions. The enclosure 11 can also include any suitable material or materials, e.g., at least one of glass, sapphire, ceramic, or metal (e.g., titanium) materials. In one or more embodiments, the substrate 12 can form one or more portions of the enclosure 11. Further, in one or more embodiments, the membrane 20 can also form a portion of the enclosure 11.

The substrate 12 of the assembly 10 can include take any suitable shape or shapes and have any suitable dimensions. Further, the substrate 12 can be a conductive substrate or a nonconductive substrate and can include any suitable material or materials, e.g., at least one of sapphire, glass, ceramic, or metallic (e.g., titanium) materials. Although depicted as monolithic, the substrate 12 can include one or more layers of the same or differing materials that can be connected together using any suitable technique or techniques. In one or more embodiments, the substrate 12 can include one or more optional layers disposed on at least one of its first major surface 14 or second major surface. As shown in FIG. 1, an optional nonconductive layer 44 is disposed on the second major surface 16 of the substrate 12. The optional nonconductive layer 44 can take any suitable shape or shapes and have any suitable dimensions. Further, the optional nonconductive layer 44 can include any suitable material or materials, e.g., the same nonconductive materials described herein for the substrate 12. The optional nonconductive layer 44 can be disposed on the second major surface 16 of the substrate 12 using any suitable technique or techniques, e.g., chemical vapor deposition, fusing bonding, brazing, soldering, glassing, etc.

Extending through the substrate 12 is the via 18. Although depicted as including a single via 18, the assembly 10 can include any suitable number of vias. The via 18 extends through the substrate 12 along the via axis 2 between the first major surface 14 and the second major surface 16 of the substrate. In one or more embodiments, the via axis 2 is substantially orthogonal to the first major surface 14 of the substrate 12. As used herein, the term "substantially orthogonal" means that the via axis 2 forms an angle with a normal to the first major surface 14 of the substrate 12 that is less than 5 degrees. The via 18 can have any suitable dimensions. In one or more embodiments, the via 18 can have a cross-sectional area in a plane orthogonal to the via axis 2 of at least 0.1 mm and no greater than 10 mm.

Further, the via 18 can take any suitable shape or shapes in the plane orthogonal to the via axis 2, e.g., rectilinear, ovular, polygonal, etc. As shown in FIG. 2, the via 18 has a circular cross-section in the plane orthogonal to the via axis. The via 18 can also take any suitable shape or shapes in a plane orthogonal to the first major surface 14 of the substrate 12 and co-planer with the via axis 2. In one or more embodiments, the via 18 has an area in the plane orthogonal to the via axis 2 that is constant along the axis. In one or more embodiments, the via 18 can have an area in the plane orthogonal to the via axis 2 that varies along the axis. For example, as shown in FIG. 1, the via 18 has an area in the orthogonal plane that decreases in a direction from the second major surface 16 of the substrate 12 to the first major surface 14. In other words, the via 18 can have one or more sloped side walls 19.

The via 18 can be formed using any suitable technique or techniques, e.g., drilling, laser drilling, etching, hot forming, etc. As is further described herein, the via 18 can be disposed through the substrate 12 before or after the membrane 20 is disposed on the first major surface 14 of the substrate. In one or more embodiments, the membrane 20 can be disposed on the substrate 12 prior to formation of the via 18 such that the membrane acts as an etch stop.

Disposed over the via 18 and on the first major surface 14 of the substrate 12 is the membrane 20. As used herein, the phrase "over the via" means that an element or component is disposed along the via axis 2 on the first major surface 14 side of the substrate 12. The membrane 20 includes the first major surface 22 and the second major surface 24, where the second major surface of the membrane is disposed on the first major surface 14 of the substrate 12. The membrane 20 can take any suitable shape or shapes and have any suitable dimensions. For example, the membrane 20 can have a thickness in a direction parallel to the via axis 2 that is at least about 1 micron and no greater than about 100 microns. The membrane 20 can be disposed over any suitable portion or portions of the first major surface 14 of the substrate 12. Although depicted as being disposed on the first major surface 14 of the substrate 12, one or more additional layers can be disposed between one or more portions of the membrane 20 and the substrate, e.g., glass, metal (e.g., titanium), silicon, etc.

The membrane 20 can include any suitable material or materials, e.g., the same materials described herein regarding the substrate 12. In one or more embodiments, the membrane 20 can include sapphire. Although depicted as two separate layers or elements, the substrate 12 and the membrane 20 can be integral, e.g., manufactured as a single part. In such embodiments, the integral substrate 12 and membrane 20 can be a single crystal sapphire material. When separate parts, the membrane 20 can be disposed on the first major surface 14 of the substrate 12 and bonded to the first major surface using any suitable technique or techniques, e.g., deposition, chemical vapor deposition, plasma vapor deposition, diffusion bonding, laser-assisted diffusion bonding, high temperature fusion bonding. In one or more embodiments, the membrane 20 can be bonded to the first major surface 14 of the substrate using one or more of the diffusion bonding techniques described in co-owned and co-filed U.S. Pat. No. 10,124,559 to Sandlin et al. and entitled KINETICALLY LIMITED NANO-SCALE DIFFUSION BOND STRUCTURES AND METHODS.

The patterned metal layer 26 can be disposed on the first major surface 22 of the membrane 20 and can include any suitable conductive material or materials, e.g., at least one of aluminum, copper, nickel, gold, transparent conductive oxide, or titanium. Further, the patterned metal layer 26 can include any suitable number of conductive layers, e.g., one, two, three, or more layers. The metal layer 26 can be disposed directly on the membrane 20. In one or more embodiments, one or more additional layers can be disposed between the metal layer 26 and the membrane 20 that include any suitable material or materials, e.g., at least one of glass, polyimide, polybenzoxazole (PBO), or nitride.

The metal layer 26 can be disposed in any suitable pattern or patterns on the membrane 20. For example, as shown in FIG. 2, which is a schematic bottom plan view of the assembly 10, the patterned metal layer 26 includes the portion 28 and a second portion 46 that is electrically connected to the first portion. The portion 28 is disposed on the membrane 20 over the via 18 along the via axis 2 and is circular in shape, while the second portion 46 of the patterned metal layer extends from the portion and electrically connects the portion to interconnect pad 48. The portion 28 of the patterned metal layer 26 provides the first capacitor plate 30 of the variable capacitor 42.

The patterned metal layer 26 can be disposed on the membrane 20 using any suitable technique or techniques, e.g., vapor deposition, chemical vapor deposition, plasma vapor deposition, physical vapor deposition, plating, atomic layer deposition, etc. Further, the metal layer 26 can be patterned using any suitable technique or techniques, e.g., etching, laser patterning, pattern plating, lift-off. In one or more embodiments, an insulating layer that includes any suitable insulating material or materials can be disposed on the patterned conductive layer 26 between the patterned conductive layer and the integrated circuit 32.

Disposed adjacent to the first major surface 22 of the membrane 20 and over the via 18 is the integrated circuit 32. As used herein, the phrase "adjacent to the first major surface of the membrane" means that an element or component is disposed closer to the first major surface 22 of the membrane 20 than to the second major surface 24 of the membrane. The integrated circuit 32 can be disposed on the membrane 20, on the patterned metal layer 26, or on both the membrane and the patterned metal layer. In one or more embodiments, one or more additional layers can be disposed between the integrated circuit 32 and at least one of the patterned metal layer 26 or the membrane 20. The integrated circuit 32 can be disposed on at least one of the membrane 20 or the patterned metal layer 26 using any suitable technique or techniques, e.g., bonding, compression bonding, low temperature laser bonding, soldering, etc.

The integrated circuit 32 can be electrically connected to the metal layer 26 using any suitable technique or techniques. In one or more embodiments, one or more interconnect pads 48 can electrically connect the patterned metal layer 26 to the integrated circuit 32. The interconnect pads 48 can include any suitable conductive contact or pad, e.g., copper pillars, solder bumps, compression-bonded metal (e.g., gold) pads, conductive-epoxy-bonded pads, etc. Further, any suitable number of interconnect pads 48 can be utilized to electrically connect the integrated circuit 32 to the patterned metal layer 26.

The integrated circuit 32 includes an integrated circuit substrate 34 having a first major surface 36 and a second major surface 38. In the embodiment illustrated in FIGS. 1-2, the second major surface 38 of the substrate 34 faces the first major surface 22 of the membrane 20. The integrated circuit 32 can include one or more electrical components disposed on at least one of the first major surface 36 or second major surface 38, or within the substrate 34. For example, the integrated circuit 32 includes one or more electrical components 50 disposed adjacent to first major surface 36 and one or more electrical components 52 disposed within the substrate 34. Any suitable electrical components 50, 52 can be utilized with the integrated circuit 32, e.g., one or more field effect transistors (FETs), metal oxide semiconductors (MOS), MOSFETs, insulated gate bipolar junction transistors (IGBT), thyristors, bipolar transistors, diodes, MOS-controlled thyristors, resistors, capacitors, etc. Further, one or more conductive layers can be disposed on at least one of the first major surface 36 or second major surface 38 of the substrate 34, or within the substrate. As shown in FIG. 1, the integrated circuit 32 includes a patterned conductive layer 54 disposed on the first major surface 36 of the substrate 34, and a second patterned conductive layer 56 disposed within the substrate. One or more of the electrical components 50, 52 can be electrically connected to other components or conductive layers 54, 56 using any suitable technique or techniques. For example, the integrated circuit 32 can include one or more vias 58 that can extend between electrical components 50, 52 and conductive layers 54, 56 to provide one or more electrical connections between such components and conductive layers. Further, one or more vias 58 can be electrically connected to one or more interconnect pads 48 to provide electrical connections between the interconnect pads and one or more electrical components 50, 52 or patterned conductive layers 54, 56 of the integrated circuit 32.

The integrated circuit 32 can also include a reference capacitor 60 disposed on or within the substrate 34. In the embodiment illustrated in FIG. 1, the reference capacitor 60 is disposed along the via axis 2. The reference capacitor 60 can include any suitable capacitor or capacitors. In one or more embodiments, the reference capacitor 60 can include a first reference capacitor plate 62 and a second reference capacitor plate 64. In one or more embodiments, the second reference capacitor plate 64 includes or provides the second capacitor plate 40 of the variable capacitor 42. The reference capacitor 60 also includes a dielectric layer 66 disposed between the first reference capacitor plate 62 and the second reference capacitor plate 64.

The first and second reference capacitor plates 62, 64 can include any suitable material or materials and be disposed on or within the substrate 34 of the integrated circuit 32 using any suitable technique or techniques. Further, the dielectric layer 66 of the reference capacitor 60 can include any suitable dielectric material or materials and be disposed between the plates 62, 64 using any suitable technique or techniques. In one or more embodiments, the dielectric layer 66 of the reference capacitor 60 can be formed by a portion of the passivation layer 68 that is disposed on the second major surface 38 of the integrated circuit substrate 34. The passivation layer 68 can include any suitable dielectric material or materials and be disposed on the second major surface 38 of the integrated circuit substrate 34 using any suitable technique or techniques.

As mentioned herein, the first capacitor plate 30 that is formed by the portion 28 of the patterned conductive layer 26 disposed on the membrane 20 along with the second capacitor plate 40 form the variable capacitor 42. The variable capacitor 42 is disposed along the via axis 2. In one or more embodiments, the first capacitor plate 30 and the second capacitor per plate 40 are substantially parallel. As used herein, the phrase "substantially parallel" means that an angle formed between the first capacitor plate 30 and the second capacitor plate 40 is less than 10 degrees. Further, the first capacitor plate 30 and the second capacitor plate 40 of the variable capacitor 42 can be spaced apart any suitable distance 70. In one or more embodiments, this space 70 between the first and second capacitor plates 30, 40 of the variable capacitor 42 can be filled with any suitable dielectric material, e.g., air, compliant polymer, urethane foam, aerogel, etc. In one or more embodiments, a vacuum could be provided within the space between the plates 30, 40. In one or more embodiments, a portion of the passivation layer 68 can be disposed between the first capacitor plate 30 and the second capacitor plate 40 to provide a dielectric material between such plates.

The second capacitor plate 40 of the variable capacitor 42 can be provided by the second reference capacitor plate 64 of the reference capacitor 60. In one or more embodiments, the second capacitor plate 40 of the variable capacitor 42 can be provided by one or more metal layers disposed on or within the integrated circuit substrate 34.

In general, the variable capacitor 42 of assembly 10 can be adapted to detect changes in pressure of an environment proximate to the second major surface 16 of the substrate 12 and the via 18 through deflection of the membrane 20 caused by these changes. In one or more embodiments, the variable capacitor 42 can be adapted to provide a first capacitance reading based upon the distance 70 between the first capacitor plate 30 and the second capacitor plate 40 as such distance changes due to deflection of the membrane 20 caused by pressure changes. The first capacitance reading can be compared to a second capacitance reading provided by the reference capacitor 60. The first capacitance reading can be compared to the second capacitance reading to determine a pressure change of the environment proximate to the second major surface 16 and the via 18 using any suitable technique or techniques, e.g., one or more techniques described in U.S. Patent Publication No. 2019/0350467 A1 to Greenhut and entitled MEASUREMENT OF CARDIAC CYCLE LENGTH AND PRESSURE METRICS FROM PULMONARY ARTERIAL PRESSURE; U.S. Pat. No. 7,955,319 B2 to Miesel and entitled PRESSURE SENSING IN IMPLANTABLE MEDICAL DEVICE; and U.S. Pat. No. 7,591,185 B1 to Mothilal et al. and entitled PRESSURE SENSOR CONFIGURATIONS FOR IMPLANTABLE MEDICAL ELECTRICAL LEADS.

Figure 4:
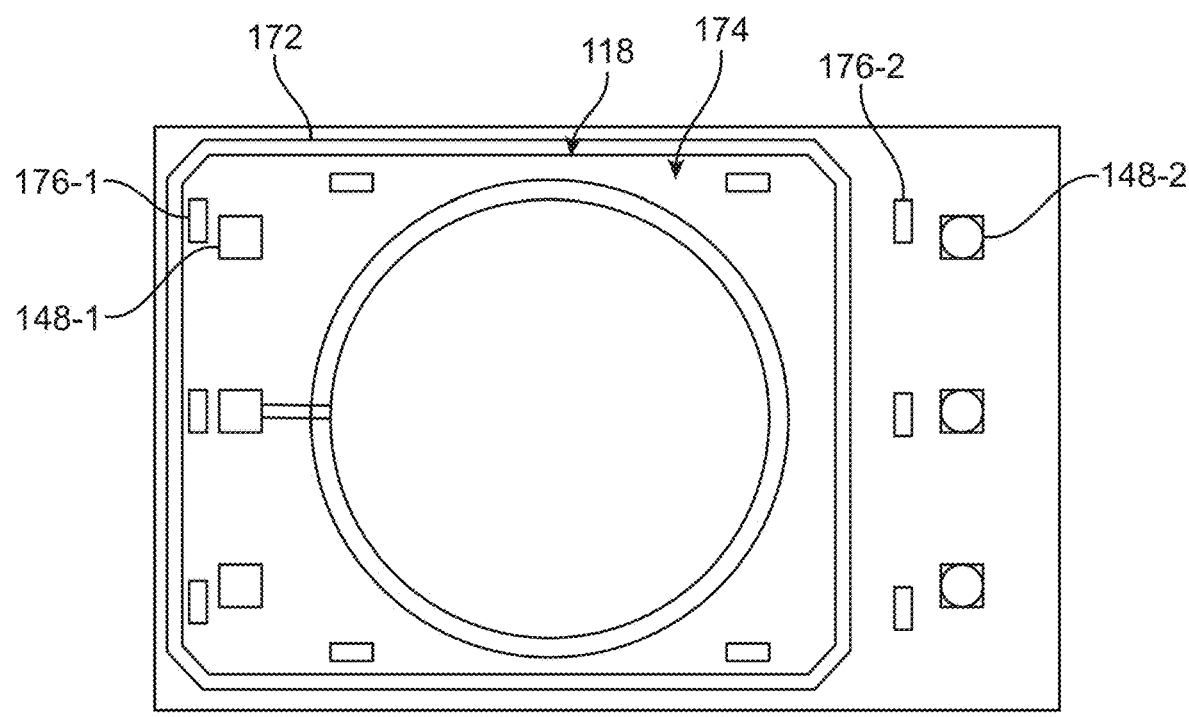
FIG. 4 is a schematic bottom plan view of the pressure sensor assembly of FIG. 3.
Figure 3:
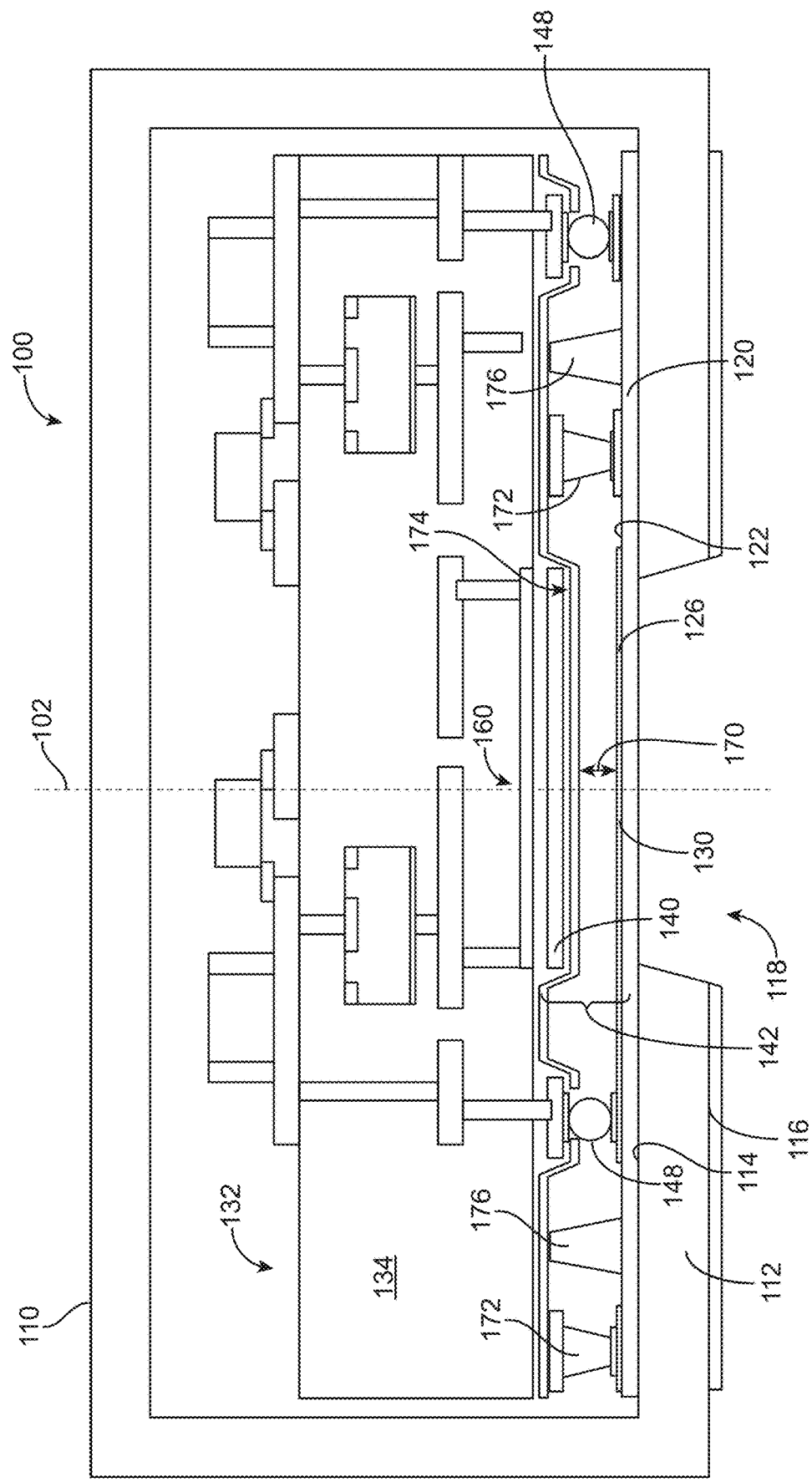
FIG. 3 is a schematic cross-section view of another embodiment of a pressure sensor assembly.

The space between the integrated circuit 32 and the membrane 20 can, in one or more embodiments, be hermetically sealed. Such hermetically-sealed space can prevent contaminants from entering the space and interfering with the function of the variable capacitor 42. Further, in such embodiments, the enclosure 11 can be removed from the assembly 10 as the space between the integrated circuit 32 and the membrane 20 is protected from intrusion by contaminants. FIGS. 3-4 are schematic cross-section and bottom plan views of another embodiment of a pressure sensor assembly 100. All of the design considerations and possibilities described herein regarding the pressure sensor assembly 10 of FIGS. 1-2 apply equally to the pressure sensor assembly 100 of FIGS. 3-4. The assembly 100 includes a substrate 112 having a first major surface 114 and a second major surface 116, where the substrate has a via 118 disposed therethrough; a membrane 120 disposed on the first major surface of the substrate, and a patterned metal layer 126 disposed on the membrane 120, where a portion of the metal layer is aligned with the via along a via axis 102 and forms a first capacitor plate 130. The assembly 100 also includes an integrated circuit 132 disposed adjacent to the first major surface 122 of the membrane 120. A second capacitor plate 140 can be disposed on or within a substrate 134 of the integrated circuit 132. The first capacitor plate 130 and the second capacitor plate 140 form a variable capacitor 142. The integrated circuit 132 also includes a reference capacitor 160 disposed on or within the integrated circuit substrate 134. The integrated circuit 132 can be electrically connected to the metal layer 126 disposed on the first major surface 122 of the membrane 120 by interconnect pads 148. The integrated circuit 132 can be disposed within housing 110. In one or more embodiments, at least one of the substrate 112 and the membrane 120 can form a portion or portions of the housing 110.

One difference between pressure sensor assembly 100 of FIGS. 3-4 and pressure sensor assembly 10 of FIGS. 1-2 is that assembly 100 includes a seal ring 172 disposed between the integrated circuit 132 and the membrane 120. The seal ring 172 can form a hermetic enclosure 174 between the membrane 120 and the integrated circuit 132. The seal ring 172 can include any suitable seal ring or rings. Further, the seal ring 172 can take any suitable shape or shapes in a plane parallel to the first major surface 114 of the substrate 112 as shown in FIG. 4. The seal ring 172 can have any suitable dimensions. For example, a thickness of the seal ring 172 measured in a plane orthogonal to the first major surface 114 of the substrate 112 can be any suitable value. In addition, the seal ring 172 can include any suitable material or materials, e.g., glass, metal, or combinations thereof. Because the seal ring 172 forms the hermetic enclosure 174, the housing 110 may not be required to protect the assembly 10 from contamination. In other words, the housing 110 may not be included with the assembly 100, or the housing 110 may not need to provide a hermetic enclosure for the pressure sensor assembly 10.

The seal ring 172 can be connected to the integrated circuit 132 and the membrane 120 using any suitable technique or techniques, e.g., plating, plasma vapor deposition, chemical vapor deposition.

Another difference between assembly 100 and assembly 10 is that assembly 100 also includes standoffs 176 that are disposed between the integrated circuit 132 and the membrane 120. Such standoffs 176 can take any suitable shape or shapes and have any suitable dimensions. For example, the standoffs 176 can have a height in a plane orthogonal to the first major surface 114 of the substrate 112 that can be selected to provide a desired spacing 170 between the first capacitor plate 130 and the second capacitor plate 140 of the variable capacitor 142. The standoffs 176 can include any suitable material or materials and be disposed between the integrated circuit 132 and the membrane 120 using any suitable technique or techniques. Further, the assembly 100 can include any suitable number of standoffs.

The seal ring 172 can be disposed in any suitable location between the integrated circuit 132 and the membrane 120. As shown in FIG. 4, the seal ring 172 encircles the via 118, interconnect pads 148-1, and standoffs 176-1. Standoffs 176-2 and interconnect pads 148-2 are disposed outside of the space surrounded by the weld ring 172 and are, therefore, not within the hermetic enclosure 174. Any suitable number of standoffs 176 and interconnect pads 148 can be disposed within the hermetic enclosure 174 and outside of the enclosure.

Figure 5:
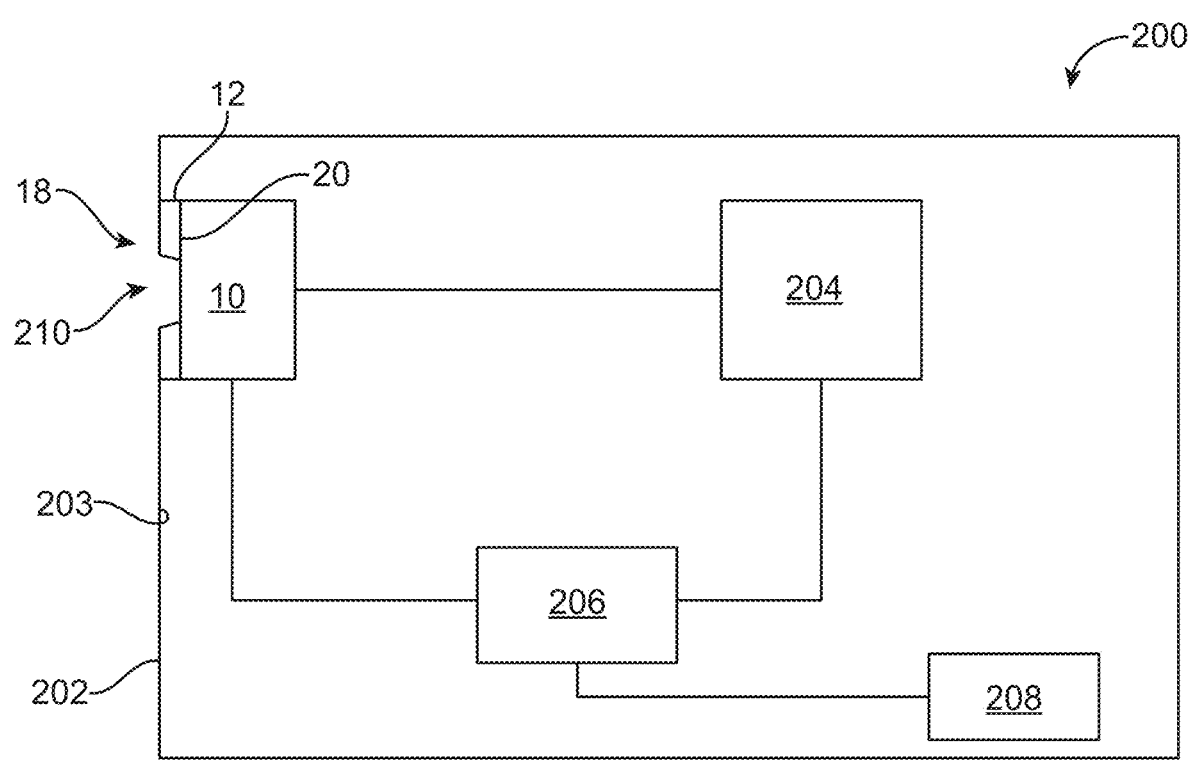
FIG. 5 is a schematic plan view of one embodiment of an implantable medical device that includes the pressure sensor assembly of FIG. 1.

As mentioned herein, the various embodiments of pressure sensor assemblies can be utilized in any suitable device or system. In one or more embodiments, the pressure sensor assembly can be utilized with a medical device that is disposed on or within a body of a patient. For example, FIG. 5 is a schematic plan view of one embodiment of an implantable medical device 200. The device 200 can include any suitable medical device that can be implanted within a body of a patient, e.g., a defibrillator that can be implanted within or exterior to a heart, a cranial device, a stent, a drug pump, a heart pump such as a left ventricular assist device (LVAD), a pulmonary device, diagnostic device, etc. Further, the device 200 can be disposed in any suitable location on or within the body of the patient, e.g., vasculature, body tissue, fluids, etc.

The implantable medical device 200 includes a housing 202 and the pressure sensor assembly 10 of FIGS. 1-2. Although described in regard to pressure sensor assembly 10, the implantable medical device 200 can include any suitable pressure sensor assembly. The device 200 can also include a power source 204 and a controller 206 each disposed at least partially within the housing 202 and electrically connected to the pressure sensor assembly 10. The controller 206 can also be electrically connected to the power source 204. In one or more embodiments, the device 200 also includes a transceiver 208 electrically connected to the controller 206 and the power source 204.

The housing 202 of the device 200 can take any suitable shape or shapes and have any suitable dimensions. Further, the housing 202 can include any suitable biocompatible material or materials, e.g., metallic, glass, ceramic, or polymeric materials. In one or more embodiments, the housing 202 includes at least one of titanium, sapphire, glass, or ceramic materials. Although shown in FIG. 5 as a unitary housing 202, the housing can include two or more portions that are connected together using any suitable technique or techniques. For example, the housing 202 can have one or more transparent portions and opaque portions that are bonded together as is described, e.g., in U.S. patent application Ser. No. 17/118,283 to Ruben et al. and entitled HERMETIC ASSEMBLY AND DEVICE INCLUDING SAME.

The housing 202 can include a port 210 that is connected to the via 18 of the pressure sensor assembly 10. The assembly 10 can be disposed on an inner surface 203 of the housing 202 such that the via is exposed to an environment external to the housing 202 through the port 210. Any suitable technique or techniques can be utilized to connect the pressure sensor assembly 10 to the inner surface 203 of the housing 202. In one or more embodiments, the substrate 12 of the assembly 10 can form a portion of the housing 202. Because the membrane 20 is hermetically sealed to the substrate 12, the via 18 and the port 210 are hermetically sealed from the external environment. The assembly 10 is, therefore, disposed such that it can detect pressure changes in the external environment through the port 210 and the via 18.

The power source 204 can include any suitable power source or sources, e.g., one or more batteries. In one or more embodiments, the power source 204 can be an internal component of a wireless energy transfer system that receives energy from an external component of the system that directs an electromagnetic field to the internal component.

Also disposed within the housing 202 is the controller 206. Such controller 206 can include any suitable electronic circuitry or components, e.g., one or more processors, memory, input devices, output devices, sensors, power sources, etc. Although not shown, the controller 206 can include any suitable memory or storage.

The controller 206 can be adapted to detect a first capacitance of the variable capacitor 42 (FIG. 1) of the pressure sensor assembly 10, detect a second capacitance of the reference capacitor 60 (also FIG. 1) of the assembly, and compare the first capacitance and the second capacitance. Such comparison can utilize any suitable technique or techniques to determine whether a pressure of the external environment has changed and if so to what extent. The comparison can provide a pressure change value that can be transmitted by the transceiver 208 to an external transceiver using any suitable technique or techniques. In one or more embodiments, the controller 206 can be adapted to determine an average pressure (e.g., in a cranium or artery of a patient), dynamic time-varying pressure (e.g., in an artery), etc.

The various embodiments of pressure sensor assemblies described herein can be manufactured using any suitable technique or techniques. For example, FIGS. 6A-F are various cross-section views of one embodiment of a method 300 of manufacturing the pressure sensor assembly 10 of FIGS. 1-2. Although described in regard to pressure sensor assembly 10, the method 300 can be utilized to manufacture any suitable pressure sensor assembly.

Figure 6A:
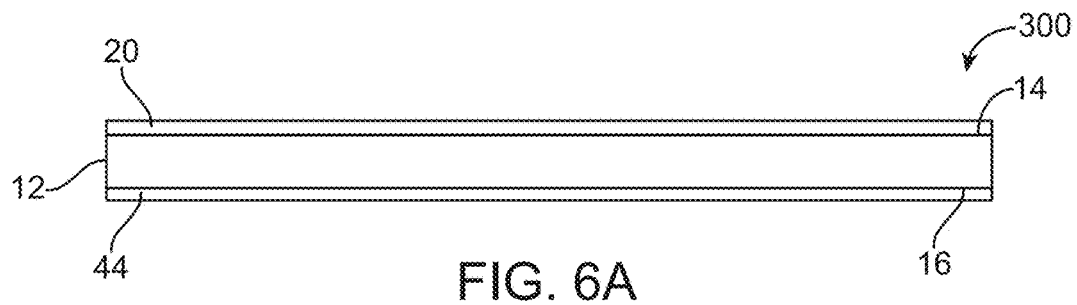
FIGS. 6A-F are schematic cross-section views of one embodiment of a method of manufacturing the pressure sensor assembly 10 of FIG. 1, where

As shown in FIG. 6A, the membrane 20 can be disposed adjacent to the first major surface 14 of the substrate 12 using any suitable technique or techniques. In one or more embodiments, the membrane 20 can be disposed on the first major surface 14 of the substrate 12. Further, in one or more embodiments, the membrane 20 can be bonded to the first major surface 14 of the substrate 12 using any suitable technique or techniques, e.g., diffusion bonding, high temperature diffusion bonding, fusing bonding, brazing, soldering, etc.

Figure 6B:
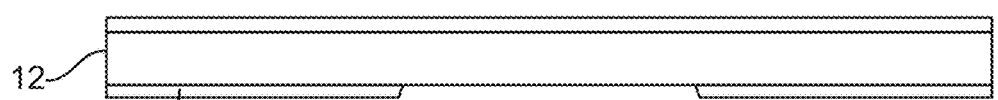

Further, optional nonconductive layer 44 can be disposed on the second major surface 16 of the substrate 12 using any suitable technique or techniques. Photoresist 302 can be disposed on the nonconductive layer 44 using any suitable technique or techniques as shown in FIG. 6B. The photoresist 302 and the nonconductive layer 44 can be patterned and etched using any suitable technique or techniques. In embodiments where the substrate 12 includes gold or silicon, and the nonconductive layer 44 includes sapphire, the substrate can act as an etch stop when etching the sapphire nonconductive layer.

Figure 6C:
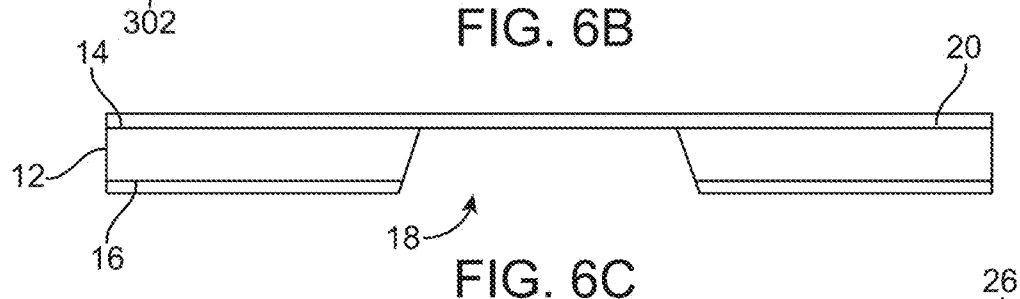

As shown in FIG. 6C, the via 18 can be disposed through the substrate 12 such that it extends along the via axis (via axis 2 of FIG. 1) between the first major surface 14 and the second major surface 16 of the substrate using any suitable technique or techniques. In one or more embodiments, the membrane 20 can act as an etch stop when forming the via 18. As a result of formation of the via 18, the membrane 20 is disposed over such via. In one or more embodiments, the nonconductive layer 44 can be disposed on the second major surface 16 of the substrate 12 prior to disposing the via 18 through the substrate such that the via extends through the nonconductive layer and the substrate.

Figure 6D:
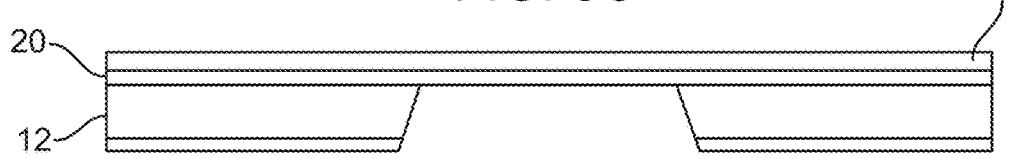
Figure 6E:
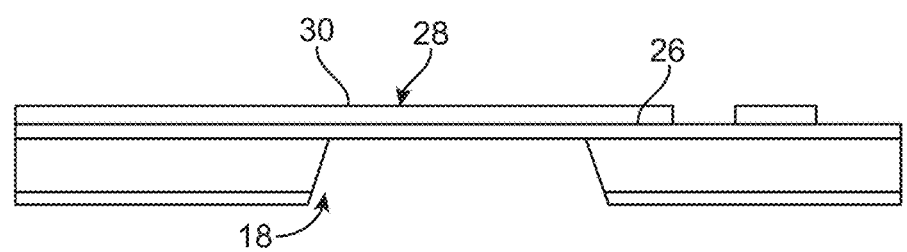

The metal layer 26 can be disposed on the membrane 20 as shown in FIG. 6D using any suitable technique or techniques such that the membrane is disposed between the metal layer and the substrate 12. In FIG. 6E, the metal layer 26 can be patterned using any suitable techniques or techniques such that the portion 28 forms the first capacitor plate 30 that is aligned with the via 18 along the via axis 2.

Figure 6F:
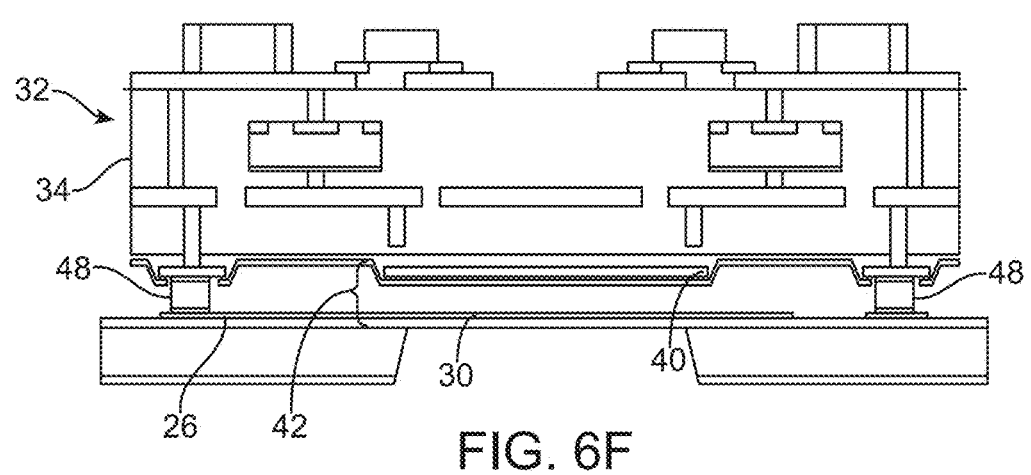

As shown in FIG. 6F, the integrated circuit 32 can be disposed adjacent to the membrane 20 and over the via 18 using any suitable technique or techniques. The integrated circuit 32 can be electrically connected to the pattern metal layer 26 using any suitable technique or techniques, e.g., interconnect pads 48 can be disposed between the integrated circuit 32 and the metal layer and connected to the integrated circuit and metal layer using any suitable techniques. In one or more embodiments, the integrated circuit 32 can be bonded to the membrane 20 using any suitable technique or techniques, e.g., thermal compression bonding, laser bonding, etc. The first capacitor plate 30 and the second capacitor plate 40 form the variable capacitor 42 disposed along the via axis.

Figure 7A:
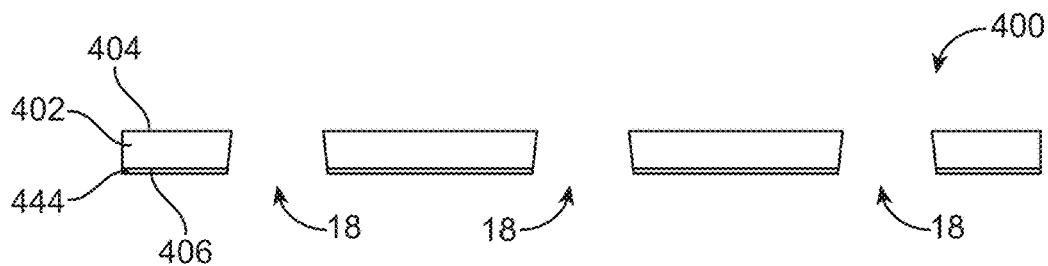
FIGS. 7A-F are schematic cross-section views of another embodiment of a method of manufacturing the pressure sensor assembly 10 of FIG. 1, where

As mentioned herein, the various embodiments of pressure sensor assemblies described herein can be formed using a wafer-to-wafer process. For example, FIGS. 7A-F are various cross-section views of one embodiment of a method 400 of forming one or more pressure sensor assemblies 10 of FIGS. 1-2 using a wafer-to-wafer process. Although described in regard to pressure sensor assembly 10 of FIGS. 1-2, the method 400 can be utilized to form any suitable pressure sensor assembly As shown in FIG. 7A, one or more vias 18 can be disposed through a substrate wafer 402 such that the vias extend along a via axis (via axis 2 of FIG. 1) between a first major surface 404 and a second major surface 406 of the substrate wafer using any suitable technique or techniques. One or more embodiments, optional nonconductive layer 444 can be disposed on the second major surface 406 of the substrate wafer 402 using any suitable technique or techniques either prior to or after the vias 18 have been formed through the substrate wafer.

Figure 7B:
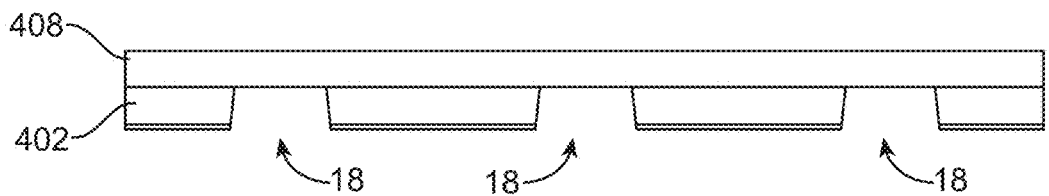
Figure 7C:
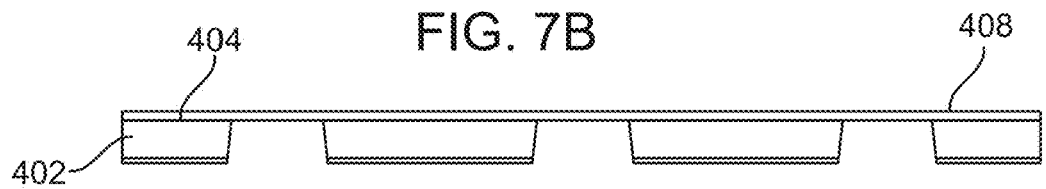

In FIG. 7B, a membrane wafer 408 is disposed on the first major surface 404 of the substrate wafer 402 and over the vias 18 using any suitable technique or techniques, e.g., the same techniques described herein regarding bonding of membrane 20 to substrate 12 as shown in FIG. 6A of method 300. In one or more embodiments, the substrate wafer 402 and the membrane wafer 408 can be a single wafer, and the membrane 20 can be formed from the single wafer. As shown in FIG. 7C, one or more portions of the membrane wafer 408 can be removed to reduce a thickness of the wafer as measured in a direction orthogonal to the first major surface 404 of the substrate wafer using any suitable technique or techniques, e.g., chemical mechanical polishing, laser ablation, grinding, etc.

Figure 7D:
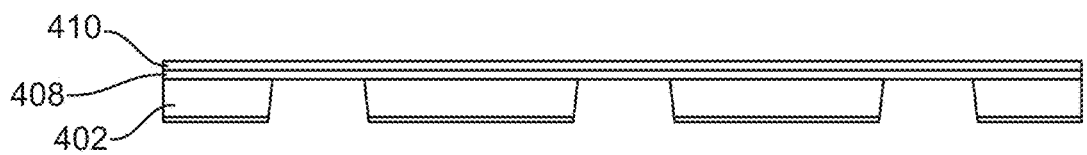
Figure 7E:
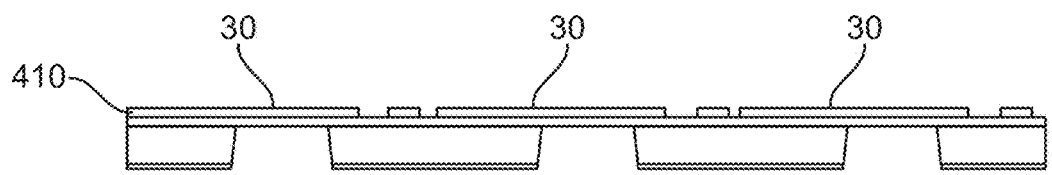

In FIG. 7D metal layer 410 can be disposed on the membrane wafer 408 using any suitable technique or techniques such that the membrane wafer is disposed between the metal layer and the substrate wafer 402. As shown in FIG. 7E, the metal layer 410 can be patterned using any suitable technique or techniques such that a portion of the metal layer provides the first capacitor plate 30 for each eventual pressure sensor assembly formed using the method 400.

Figure 7F:
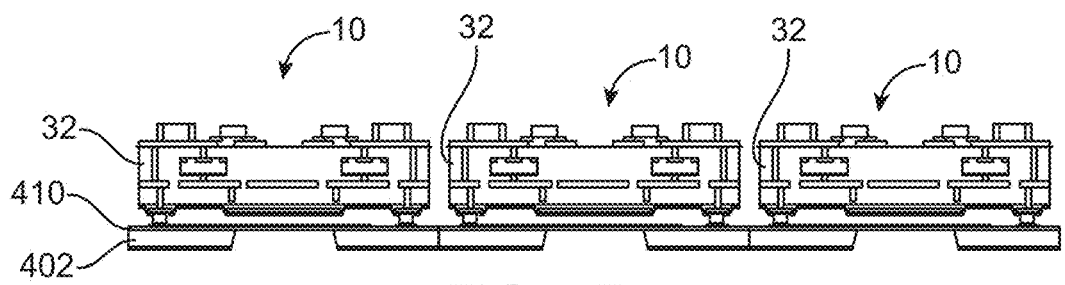

One or more integrated circuits 32 can be disposed adjacent to the membrane wafer 408 and over the vias 18 using any suitable technique or techniques as shown in FIG. 7F. The integrated circuits 32 can be electrically connected to the patterned metal layer 410 using any suitable technique or techniques. Further, the substrate wafer 402 and the membrane wafer 408 can be singulated using any suitable technique or techniques to provide one or more pressure sensor assemblies 10.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A pressure sensor assembly comprising:
   a substrate comprising a via that extends through the substrate along a via axis between a first major surface and a second major surface of the substrate, wherein the via axis is substantially orthogonal to the first major surface of the substrate;
   a membrane comprising a first major surface and a second major surface, wherein the second major surface of the membrane is disposed on the first major surface of the substrate and over the via;
   a patterned metal layer disposed on the first major surface of the membrane, wherein a portion of the metal layer aligned with the via along the via axis comprises a first capacitor plate; and
   an integrated circuit disposed adjacent to the first major surface of the membrane and over the via, wherein the integrated circuit is electrically connected to the metal layer disposed on the first major surface of the membrane, wherein the integrated circuit comprises an integrated circuit substrate comprising a first major surface and a second major surface, and a second capacitor plate disposed on or within the substrate, wherein the second capacitor plate is substantially parallel to and spaced apart from the first capacitor plate disposed on the membrane;
   wherein the first capacitor plate and the second capacitor plate form a variable capacitor disposed along the via axis.

2. The assembly of claim 1, wherein the second capacitor plate is disposed on the second major surface of the integrated circuit substrate that faces the first major surface of the membrane.

3. The assembly of claim 1, wherein the integrated circuit further comprises a reference capacitor comprising a first reference capacitor plate, a second reference capacitor plate, and a dielectric layer disposed between the first reference capacitor plate and the second reference capacitor plate.

4. The assembly of claim 3, wherein the second reference capacitor plate comprises the second capacitor plate of the variable capacitor.

5. The assembly of claim 3, wherein the dielectric layer of the reference capacitor is formed by a portion of a passivation layer that is disposed on the second major surface of the integrated circuit substrate.

6. The assembly of claim 1, further comprising a seal ring disposed between the integrated circuit and the membrane, wherein the seal ring forms a hermetic enclosure between the membrane and the integrated circuit.

7. The assembly of claim 1, further comprising a nonconductive layer disposed on the second major surface of the substrate, wherein the via is disposed through the nonconductive layer and the substrate.

8. The assembly of claim 1, further comprising one or more interconnect pads disposed adjacent to the first major surface of the integrated circuit substrate.

9. The assembly of claim 1, wherein the membrane is bonded to the first major surface of the substrate.

10. An implantable medical device comprising:
   a housing; and
   a pressure sensor assembly comprising:
      a substrate comprising a via that extends through the substrate along a via axis between a first major surface and a second major surface of the substrate, wherein the via axis is substantially orthogonal to the first major surface of the substrate;
      a membrane comprising a first major surface and a second major surface, wherein the second major surface of the membrane is disposed on the first major surface of the substrate and over the via;
      a patterned metal layer disposed on the first major surface of the membrane, wherein a portion of the metal layer aligned with the via along the via axis comprises a first capacitor plate; and
      an integrated circuit disposed adjacent to the first major surface of the membrane and over the via, wherein the integrated circuit is electrically connected to the metal layer disposed on the first major surface of the membrane, wherein the integrated circuit comprises an integrated circuit substrate comprising a first major surface and a second major surface, and a second capacitor plate disposed on or within the substrate, wherein the second capacitor plate is substantially parallel to and spaced apart from the first capacitor plate disposed on the membrane;
      wherein the first capacitor plate and the second capacitor plate form a variable capacitor disposed along the via axis.

11. The device of claim 10, further comprising a power source disposed within the housing and electrically connected to the pressure sensor assembly.

12. The device of claim 10, wherein the integrated circuit of the pressure sensor assembly further comprises a reference capacitor comprising a first reference capacitor plate, a second reference capacitor plate, and a dielectric layer disposed between the first reference capacitor plate and the second reference capacitor plate.

13. The device of claim 12, wherein the second reference capacitor plate comprises the second capacitor plate of the variable capacitor.

14. The device of claim 12, wherein the dielectric layer of the reference capacitor is formed by a portion of a passivation layer that is disposed on the second major surface of the integrated circuit substrate.

15. The device of claim 12, further comprising a controller electrically connected to the pressure sensor assembly, wherein the controller is adapted to:
   detect a first capacitance of the variable capacitor of the pressure sensor assembly;
   detect a second capacitance of the reference capacitor of the pressure sensor assembly; and
   compare the first capacitance and the second capacitance.

16. A method comprising:
   disposing a membrane adjacent to a first major surface of a substrate;
   disposing a via through the substrate such that it extends along a via axis between the first major surface and a second major surface of the substrate, wherein the membrane is disposed over the via, and further wherein the via axis is substantially orthogonal to the first major surface of the substrate;
   disposing a metal layer on the membrane such that the membrane is disposed between the metal layer and the substrate;
   patterning the metal layer such that a portion of the metal layer forms a first capacitor plate that is aligned with the via along the via axis; and
   disposing an integrated circuit adjacent to the membrane and over the via, wherein the integrated circuit is electrically connected to the metal layer, and further wherein the integrated circuit comprises an integrated circuit substrate comprising a first major surface and a second major surface, and a second capacitor plate disposed on or within the substrate, wherein the second capacitor plate is substantially parallel to and spaced apart from the first capacitor plate disposed on the membrane;
   wherein the first capacitor plate and the second capacitor plate form a variable capacitor disposed along the via axis.

17. The method of claim 16, further comprising disposing a nonconductive layer on the second major surface of the substrate.

18. The method of claim 17, wherein the nonconductive layer is disposed on the second major surface of the substrate prior to disposing the via through the substrate such that the via extends through the nonconductive layer and the substrate.

19. The method of claim 16, wherein disposing the membrane comprises bonding the membrane to the first major surface of the substrate.

20. The method of claim 19, wherein bonding the membrane comprises high temperature fusion bonding the membrane to the first major surface of the substrate.

\* \* \* \* \*